United States Patent [19]

Bart et al.

[11] 4,061,680

[45] Dec. 6, 1977

[54] METHOD OF PRODUCING HIGH-BOILING BYPRODUCTS OF ISOPRENE PRODUCTION

[76] Inventors: Evgeny Vasilievich Bart, prospekt Morisa Toreza, 18, kv. 69; Oleg Efimovich Batalin, ulitsa Ordzhonikidze, 45, korpus 1, kv. 85, both of Leningrad; Andrian Petrovich Troitsky, ulitsa Miklukho-Maklaya, 65, korpus 2, kv. 48; Nina Andreevna Skachkova, Scherbakovskaya ulitsa, 7, kv. 31, both of Moscow; Vladimir Mikhailovich Lebedev, Jubileiny prospekt, 30, kv. 98, Khimiki Moskovskoi oblasti; Rimma Petrovna Trifonova, Scherbakovskaya ulitsa, 9, kv. 102, Moscow, all of U.S.S.R.

[21] Appl. No.: 563,951

[22] Filed: Apr. 1, 1975

[51] Int. Cl.[2] .................... C07C 47/04; C07C 11/08; C07C 11/18

[52] U.S. Cl. ................ 260/606; 260/677 R; 260/681

[58] Field of Search ................ 260/606, 677 R, 681

[56] References Cited

U.S. PATENT DOCUMENTS 3,057,923  10/1962  Hellen et al. .................. 260/606

*Primary Examiner*—James O. Thomas, Jr.
*Assistant Examiner*—W. B. Lone
*Attorney, Agent, or Firm*—Fleit & Jacobson

[57] ABSTRACT

A method of processing high-boiling byproducts of isoprene production obtained at the first stage of isoprene production by the dioxane method into isoprene, isobutylene and formaldehyde which comprises the catalytic splitting of said products in the vapor phase in the presence of water with a weight ratio therebetween of $1:1 \div 2$, respectively, at 250–290° C over aluminum oxide as catalyst. The resulting vapor mixture is catalytically split at 315°–360° C over calcium-phosphate catalyst with the formation of a reaction mixture containing isoprene, isobutylene and formaldehyde.

1 Claim, No Drawings

METHOD OF PRODUCING HIGH-BOILING BYPRODUCTS OF ISOPRENE PRODUCTION

The present invention relates to methods of processing high-boiling byproducts of isoprene production into isoprene, isobutylene and formaldehyde, and more specifically it concerns a method of processing high-boiling byproducts of isoprene production obtained at the first stage of isoprene production by the dioxane method.

Isoprene, isobutylene and formaldehyde are widely used in the manufacture of synthetic rubbers and other chemical products.

At the first stage of isoprene production by the dioxane method a reaction mixture is obtained which contains dimethyldioxane, as well as high-boiling byproducts distributed among the organic and aqueous layers of the reaction mixture.

A number of methods of processing such high-boiling byproducts of isoprene production are known. Thus, it is known to subject these products to hydrolysis in the presence of inorganic acids. Service problems, however, arise in developing the production method for such processes associated with the requirements of continuous operation of a plant and burning the resinous residues or wastes containing an inorganic acid.

It is also known to process high-boiling byproducts of isoprene production on the basis of their catalytic splitting in the vapour phase over solid catalysts at elevated temperature.

One of these methods involves the processing of high-boiling byproducts of isoprene production over a catalyst of the aluminosilicate type. By this method, high-boiling byproducts contained in the aqueous layer of the reaction mixture of dimethyldioxane synthesis (the first stage of isoprene production by the dioxane method) are fed for splitting without preliminary isolation from water, the organic layer of high-boiling byproducts being also fed for splitting. This method features a very low yield of isoprene which is only about 12% of theory.

It is also known to process high-boiling byproducts, their components or mixtures thereof with dimethyldioxane over calcium-phosphate catalyst. The process is conducted at about 350° C with a ratio of high-boiling byproducts to water of 1:3. The main disadvantage of this method consists in a rapid coking of calcium-phosphate catalyst having a very developed surface and a large void volume. A long-term burning out of coke is required for recovery of the catalyst surface so that this method is rather inefficient. The yield of isoprene by this method is comparatively low.

It is an object of the invention to provide a method of processing high-boiling byproducts of isoprene production obtained at the first stage of isoprene production by the dioxane method which permits the achievement of an improved yield of isoprene.

With this and other objects in view, the invention consists in the provision of a method of processing high-boiling byproducts of isoprene production, wherein said high-boiling byproducts are catalytically split in the vapour phase in the presence of water with a ratio therebetween of 1:1+2, respectively, over a solid catalyst, and wherein, according to the invention, the catalytic of said high-boiling byproducts is conducted over aluminum oxide as catalyst at 250°–290° C to obtain a vapour mixture which is subsequently subjected to a catalytic splitting at 315°–360° C over calcium-phosphate catalyst with the formation of a reaction mixture containing isoprene, isobutylene and formaldehyde.

As mentioned above, high-boiling byproducts formed at the first stage of the process in preparing dimethyldioxane in isoprene production from formaldehyde and isobutylene comprise a complex mixture of various compounds exhibiting different chemical properties and reactivity. This includes three isomers of dioxane alcohols, pyran compounds, numerous ethers, as well as various formals of cyclic and linear structure and unidentified compounds especially including numerous heavy fractions boiling above the boiling point of dioxane alcohols.

Our studies show that at the present state of the art no satisfactory result can be obtained using any single catalyst in any single-stage process.

Thus, the catalytic splitting of high-boiling byproducts over aluminum oxide results in obtaining a negligible quantity of isoprene, isobutylene and a high yield of the total of unsaturated alcohols, formaldehyde, pyran compounds, etc. (see Tables 1 and 2).

TABLE 1

| | CONDITIONS OF PROCESSING HIGH-BOILING BYPRODUCTS OVER ALUMINUM OXIDE CATALYST | | | | |
|---|---|---|---|---|---|
| | Temperature in the catalyst column, °C | | | High-boiling | Rate of feeding of high-boiling products, |
| Catalyst | top | middle | bottom | byproducts/ water ratio | g/h per g of catalyst |
| Aluminum oxide | 266 | 254 | 254 | 1:2 | 2.0 |

TABLE 2

| | | YIELDS OF PRODUCTS IN SPLITTING HIGH-BOILING BYPRODUCTS OVER ALUMINUM OXIDE CATALYST UNDER THE CONDITIONS SHOWN IN TABLE 1 | | | | | | | | |
|---|---|---|---|---|---|---|---|---|---|---|
| Starting high-boiling byproducts Components | Content of test mixture, g | Reaction mixture | | | | | Converted | | | Yield % of conversion of high-boiling byproducts |
| | | | Reaction products obtained | | | | | | | |
| | | | Organic layer, g | Aqueous layer, g | Gas, g | Total, g | g | % | g | |
| 1 | 2 | 3 | 4 | 5 | 6 | 7 | 8 | 9 | 10 | 11 |
| | | Carbon dioxide | — | — | 2.37 | 2.37 | | | 2.37 | 1.02 |
| | | Carbon oxide | — | — | 0.27 | 0.27 | | | 0.27 | 0.12 |
| | | Isobutylene | 2.52 | — | 13.30 | 15.82 | | | 15.32 | 6.85 |
| | | Isoprene | 10.22 | — | 5.20 | 15.42 | | | 15.42 | 6.65 |
| | | Methanol | — | 14.35 | — | 14.35 | | | 14.35 | 6.19 |
| | | Trimethylcarbinol | 1.79 | 8.39 | — | 10.18 | | | 10.18 | 4.39 |
| Unsaturated alcohols C$_5$ | 6.48 | Unsaturated alcohols C$_5$ | 28.61 | 22.30 | — | 50.91 | | | 44.43 | 19.15 |
| | | Methylenetetrahydropyran | 4.42 | 1.36 | | 5.78 | | | 5.78 | 2.5 |
| | | Methyldihydropyran | 12.45 | 4.68 | — | 17.13 | | | 17.13 | 7.38 |
| | | p-Xylene | 0.17 | — | — | 0.17 | | | 0.17 | 0.07 |
| | | Dimethyldioxane | 5.58 | 10.50 | — | 16.08 | | | 16.08 | 6.93 |

TABLE 2-continued
YIELDS OF PRODUCTS IN SPLITTING HIGH-BOILING BYPRODUCTS OVER ALUMINUM OXIDE CATALYST UNDER THE CONDITIONS SHOWN IN TABLE 1

| Starting high-boiling byproducts Components 1 | Content of test mixture, g 2 | Reaction mixture Reaction products obtained 3 | Organic layer, g 4 | Aqueous layer, g 5 | Gas, g 6 | Total, g 7 | Converted g 8 | Converted % 9 | g 10 | Yield % of conversion of high-boiling byproducts 11 |
|---|---|---|---|---|---|---|---|---|---|---|
| Methylvinyldioxane | 1.53 | Methylvinyl-dioxane | — | — | — | — | 1.53 | 100.0 | — | — |
| Methylbutandiol ethers | {4.86 \\ 1.08 | Methylbutan-diol ethers | {3.95 \\ — | 2.72 \\ 1.51 | | 6.67 \\ 1.51 | — \\ — | — \\ — | 1.81 \\ 0.43 | 0.78 \\ 0.19 |
| Pyran alcohol | 7.26 | Pyran alcohol | 0.79 | 8.01 | | 8.80 | — | — | 1.54 | 0.67 |
| Methylbutandiol | 35.22 | Methylbutandiol | 0.37 | 4.69 | | 5.06 | 30.16 | 85.5 | — | — |
| Dioxane alcohol ethers | 13.35 | Dioxane alcohol ethers | 4.57 | 1.44 | | 6.01 | 7.34 | 54.2 | — | — |
| Dioxane alcohol formals | 10.26 | Dioxane alcohol formals | 0.34 | 1.13 | | 1.47 | 8.79 | 86.0 | — | — |
| Dioxane alcohols | 122.07 | Dioxane alcohols | 5.48 | 14.19 | | 19.67 | 102.4 | 79.4 | — | — |
| Total of unidentified products | 8.91 | Total of unidentified products | 15.25 | 4.54 | | 19.79 | — | — | 10.88 | 4.70 |
| Heavy products boiling above dioxane alcohols | 85.41 | Unidentified heavy products | 3.82 | — | | 3.82 | 81.59 | 95.5 | — | — |
| Total of high-boiling byproducts in the test | 296.43 | | — | — | | | | | | |
| | | Formaldehyde | 7.05 | 53.29 | | 60.34 | — | — | 60.34 | 6.03 |
| Water | 603.57 | Water | 7.42 | 602.9 | | 610.32 | | | 6.75 | 2.92 |
| | | Losses and coke | — | — | — | 8.06 | | | 8.06 | 3.48 |
| Total | 900.0 | Total | 114.8 | 756.0 | 21.14 | 900.0 | 231.81 | 77.3 | 231.81 | 100.0 |

The basic part of the mixture obtained after the splitting may not be directly used (without separation) for the production of isoprene. In separating such mixture, e.g. by a rectification reformation of some starting compounds present in the high-boiling byproducts may take place, mainly due to water and formaldehyde addition at double bonds (Prince reaction).

The employment of calcium-phosphate catalyst for direct splitting high-boiling byproducts also cannot give desired results (see Tables 3 and 4).

TABLE 3
CONDITIONS OF PROCESSING HIGH-BOILING BYPRODUCTS OVER CALCIUM-PHOSPHATE CATALYST

| Catalyst | Temperature, °C | High-boiling byproducts/water ratio | Feeding rate of high-boiling byproducts, g/h per 1 g of catalyst |
|---|---|---|---|
| Calcium-phosphate catalyst | 320–325 | 1:2 | 1.0 |

TABLE 4
YIELDS OF PRODUCTS IN SPLITTING HIGH-BOILING BYPRODUCTS OVER CALCIUM-PHOSPHATE CATALYST UNDER THE CONDITIONS SHOWN IN TABLE 3

| Starting high-boiling byproducts Components 1 | Content of test mixture, g 2 | Reaction mixture Reaction products obtained 3 | Organic layer, g 4 | Aqueous layer, g 5 | Gas, g 6 | Total, g 7 | Converted g 8 | Converted % 9 | g 10 | Yield % of conversion of high-boiling byproducts 11 |
|---|---|---|---|---|---|---|---|---|---|---|
| | | Carbon dioxide | — | — | 0.91 | 0.91 | — | — | 0.91 | 0.02 |
| | | Carbon oxide | — | — | 0.23 | 0.23 | — | — | 0.23 | 0.16 |
| | | Isobutylene | 3.43 | — | 1.50 | 4.93 | — | — | 4.93 | 3.34 |
| | | Isoprene | 23.18 | — | 1.83 | 25.01 | — | — | 25.01 | 16.90 |
| | | Methanol | 6.06 | 0.88 | | 6.94 | — | — | 6.94 | 4.70 |
| | | Trimethylcarbinol | 0.35 | 1.37 | | 1.72 | — | — | 1.72 | 1.17 |
| Unsaturated alcohols $C_5$ | 3.67 | Unsaturated alcohols $C_5$ | 2.20 | 0.71 | | 2.91 | 0.76 | 20.7 | — | — |
| | | Methylenetetrahydropyran | 1.27 | — | | 1.27 | — | — | 1.27 | 0.86 |
| | | Methylidihydropyran | 6.43 | 0.35 | | 6.78 | — | — | 6.78 | 4.58 |
| | | p-Xylene | 0.48 | — | | 0.48 | — | — | 0.48 | 0.32 |
| | | Dimethyldioxane | 2.23 | 1.63 | | 3.86 | — | — | 3.86 | 2.51 |
| | | Methylvinyldioxane | 0.72 | — | | 0.72 | — | — | 0.72 | 0.49 |
| Methylbutandiol ethers | 2.68 | Methylbutandiol ethers | {— \\ — | 1.19 \\ 0.57 | | 1.19 \\ 0.57 | 1.49 \\ — | 55.5 \\ — | — \\ 0.57 | — \\ 0.39 |
| Pyran alcohol | 4.41 | Pyran alcohol | 0.51 | 1.46 | | 1.97 | 2.47 | 55.3 | — | — |
| Methylbutandiol | 21.96 | Methylbutandiol | 0.40 | 1.06 | | 1.46 | 20.50 | 93.5 | — | — |
| Dioxane alcohol ethers | 7.52 | Dioxane alcohol ethers | 2.19 | 1.01 | | 3.20 | 4.32 | 57.5 | — | — |
| Dioxane alcohol formals | 5.37 | Dioxane alcohol formals | 0.45 | 0.97 | | 1.42 | 3.95 | 73.5 | — | — |
| Dioxane alcohols | 67.70 | Dioxane alcohols | 0.45 | 11.29 | | 11.74 | 55.96 | 82.5 | — | — |
| Total of unidentified compounds | 6.17 | Total of unidentified compounds | 15.91 | 0.13 | | 16.04 | — | — | 9.87 | 5.56 |
| Heavy components boiling above dioxane alcohols | 58.34 | Heavy unidentified components | 0.51 | — | | 0.51 | 57.80 | 99.0 | — | — |
| Total of high-boiling byproducts | 177.82 | — | | | | | | | | |
| Water | 362.18 | Water | 1.80 | 390.05 | | 391.85 | — | — | 29.67 | 20.25 |
| | | Formaldehyde | 2.33 | 28.36 | | 30.69 | — | — | 30.69 | 20.75 |

TABLE 4-continued

YIELDS OF PRODUCTS IN SPLITTING HIGH-BOILING BYPRODUCTS OVER CALCIUM-PHOSPHATE CATALYST UNDER THE CONDITIONS SHOWN IN TABLE 3

| Starting high-boiling byproducts Components | Content of test mixture, | | Reaction mixture | | | | Converted | | | Yield % of conversion of high-boiling byproducts |
|---|---|---|---|---|---|---|---|---|---|---|
| | | | Reaction products obtained | | | | | | | |
| | | | Organic layer, g | Aqueous layer, g | Gas, g | Total, g | g | % | g | |
| 1 | 2 | 3 | 4 | 5 | 6 | 7 | 8 | 9 | 10 | 11 |
| | | Coke and losses | | | | 23.60 | | | 23.60 | 16.00 |
| Total | 540.0 | Total | 70.9 | 441.0 | 4.47 | 540.0 | 147.25 | 83.1 | 147.25 | 100.0 |

Table 3

| | Primary Skin Irritation Test | |
|---|---|---|
| Sample | Animal Test | Human Body Test |
| 1. This invention (Example 1) | 0.00 | 0/50 |
| 2. Squalane | 0.00 | 0/50 |
| 3. Unpurified polymer | 0.62 | 1/50 |

While the isoprene yield is higher here than in the case of using aluminum oxide, the yields of other valuable products, such as isobutylene and formaldehyde, are rather insufficient. But an important result is that with the direct processing of high-boiling byproducts over calcium-phosphate catalyst having a fine-porous structure the coke formation is materially increased. The yield of coke and losses attains 16%. This fact itself does not permit the use of this catalyst for decomposition of high-boiling byproducts.

However, it has been found that the successive operation with the two catalysts effected the elimination of the difficulties encountered where they are used separately. As a result of splitting of high-boiling byproducts over aluminum oxide, a vapour mixture with a low content of isoprene is obtained. This permits the carrying out of a rather deep conversion process without any risk of occurrence of secondary reactions. The splitting of the resulting vapour mixture which thus contains a negligible quantity of high-molecular compounds over calcium-phosphate catalyst permits the elimination of a rapid coking of the catalyst and results in the formation of a reaction mixture containing isoprene, isobutylene and formaldehyde so that the rectification of this mixture is not associated with losses of valuable products in the course of chemical reactions.

Thus, by conducting a successive splitting of high-boiling byproducts over aluminum oxide and calcium-phosphate catalysts isoprene, as well as isobutylene and formaldehyde can be obtained from high-boiling by-products in a comparatively high yield. The yield of isoprene in converting high-boiling byproducts ranges from 22 to 23%, formaldehyde — 25% and isobutylene — 7%. The method according to the invention permits the complete processing of high-boiling byproducts without discharging any fraction thereof due to recycle of unconverted heavy components contained in the starting products and heavy reaction products. The method may be effected using standard equipment employed in isoprene production from formaldehyde and isobutylene.

The process may be conducted in a continuous manner.

The method according to the invention is effected as follows.

For splitting high-boiling byproducts the use was made of an installation comprising an evaporator, two reactors, conventional condensation apparatus, cooling apparatus, apparatus for catching light fractions, for receiving gas and liquid products.

For the conduct of the process the temperature and rate of delivery of starting products are selected to ensure a sufficient rate of the process so as to make it more economical and, on the other hand, so as to eliminate the development of undesired secondary conversions. In addition, the secondary conversions are hindered by diluting the reaction mixture with steam so that an excessive amount of water should be fed into the installation for normal operation of the both reactors.

Starting high-boiling byproducts and water in a selected weight ratio are fed by means of a metering pump into a heated evaporator. Then the resulting vapours are fed into a reactor containing aluminum oxide, wherein the mixture is catalytically split at a preselected temperature. The resulting vapour mixture is then admitted into a reactor charged with calcium-phosphate catalyst for further catalytic conversion and then into the condensation and receiving apparatus. As a result, a reaction mixture is obtained which contains isoprene, isobutylene and formaldehyde. The liquid and gaseous products thus obtained are measured, separated and analyzed.

With continuous operation of the installation two reactor systems are used which are alternately switch-over for processing the starting products and for regeneration of the catalysts. The desired products are isolated from the reaction mixture by known methods, such rectification, and the residue is recycled for secondary processing together with the starting high-boiling byproducts.

The present invention will be better understood from the following specific examples.

EXAMPLE 1

30 g of aluminum oxide were charged into the first reactor. 60 g of calcium-phosphate catalyst were charged into the second reactor. The conditions of high-boiling by-products splitting, which are carried out under atmospheric pressure, are given in Table 5 and the resulting products yields are given in Table 6.

TABLE 5

CONDITIONS OF PROCESSING HIGH-BOILING BYPRODUCTS OVER ALUMINUM OXIDE AND CALCIUM PHOSPHATE CATALYSTS

| Reactor in the flow direction of high-boiling byproducts vapours | Temperature in the catalyst column, °C. | | | High-boiling byproducts/ water weight ratio | Rate of feeding high-boiling byproducts g/h per 1 g of catalyst |
|---|---|---|---|---|---|
| | top | middle | bottom | | |
| 1st reactor with aluminum oxide | 253 | 243 | 280 | 1:2 | 2.0 |
| 2nd reactor with calcium -phosphate catalyst | 317 | 324 | 340 | 1:2 | 1.0 |

TABLE 6
YIELDS OF PRODUCTS IN SPLITTING HIGH-BOILING BYPRODUCTS OVER ALUMINUM OXIDE AND CALCIUM-PHOSPHATE CATALYSTS UNDER THE CONDITIONS SHOWN IN TABLE 5

| Starting high-boiling byproducts | | Reaction mixture | | | | | | | Yield of products | |
|---|---|---|---|---|---|---|---|---|---|---|
| | Content in the mix used for tests, g | | Reaction products obtained | | | | Converted | | | % of conversion of byproducts |
| Components | | Components | Organic layer, g | Aqueous layer, g | Gas, g | Total, g | | | g | |
| 1 | 2 | 3 | 4 | 5 | 6 | 7 | 8 | 9 | 10 | 11 |
| | | Carbon dioxide | | | 2.27 | 2.27 | | | 2.27 | 1.42 |
| | | Carbon oxide | | | 0.55 | 0.55 | | | 0.55 | 0.84 |
| | | Isobutylene | 5.92 | — | 6.22 | 12.14 | | | 12.14 | 7.59 |
| | | Amylenes | 1.38 | — | — | 1.38 | | | 1.38 | 0.86 |
| | | Isoprene | 34.47 | — | 1.46 | 35.93 | | | 35.93 | 22.46 |
| | | Methanol | 2.76 | 9.92 | — | 12.68 | | | 12.68 | 7.92 |
| | | Trimethylcarbinol | 0.40 | 2.69 | — | 3.09 | | | 3.09 | 1.93 |
| Unsaturated alcohols $C_5$ | 3.67 | Unsaturated alcohols $C_5$ | 2.14 | 2.06 | — | 4.2 | | | 0.53 | 0.33 |
| | | Methylenetetra-hydropyran | 1.62 | 1.03 | — | 2.65 | | | 2.65 | 1.66 |
| | | Methylhydropyran | 10.52 | 0.90 | — | 11.42 | | | 11.42 | 7.15 |
| | | p-Xylene | 0.30 | — | — | 0.30 | | | 0.30 | 0.19 |
| | | Dimethyldioxane | 2.99 | 3.14 | — | 6.13 | | | 6.13 | 3.84 |
| | | Methylvinyldioxane | 0.57 | — | — | 0.57 | | | 0.57 | 0.36 |
| Methylbutandiol ethers | 2.68 | Methylbutandiol ethers | — | 0.94 | — | 0.94 | 1.74 | 65.0 | — | — |
| | | | | 0.32 | — | 0.32 | | | 0.32 | 0.20 |
| Pyran alcohol | 4.41 | Pyran alcohol | 0.26 | 1.26 | — | 1.52 | 2.89 | 65.5 | — | — |
| Methylbutandiol | 21.96 | Methylbutandiol | 0.38 | 2.11 | — | 2.49 | 19.47 | 89.0 | — | — |
| Dioxane alcohol ethers | 7.52 | Dioxane alcohol ethers | 0.70 | 0.67 | — | 1.37 | 6.15 | 81.6 | — | — |
| Dioxane alcohol formals | 5.37 | Dioxane alcohol formals | 0.47 | 0.49 | — | 0.96 | 4.41 | 82.1 | — | — |
| Dioxane alcohols | 67.70 | Dioxane alcohols | 0.47 | 0.27 | — | 0.74 | 66.96 | 98.5 | — | — |
| Total of unidentified compounds | 6.18 | Total of unidentified products | 7.47 | 1.92 | — | 9.39 | | 48.5 | 3.21 | 4.55 |
| Heavy unidentified products | 58.33 | Heavy unidentified products | 4.05 | — | — | 4.05 | 54.28 | 93.0 | — | — |
| Total of high-boiling byproducts | 177.82 | Formaldehyde | 2.16 | 38.0 | — | 40.16 | — | — | 40.16 | 25.1 |
| Water | 362.18 | Water | 0.57 | 382.88 | — | 383.45 | — | — | 21.27 | 13.29 |
| | | Losses | — | — | — | 1.3 | | | 1.3 | 0.81 |
| Total | 540.00 | Total | 79.6 | 448.6 | 10.5 | 540.0 | 155.90 | 89.5 | 155.90 | 100.0 |

It is clear from the above-given data that only 4.2 g of unsaturated alcohols or 4.2/540 100 = 0.78 w.% are present in the reaction mixture (organic and water layers). The quantity cannot have any appreciable effect on the results by a rectification even if all unsaturated alcohols react with formaldehyde.

At the same time, the reslults given above show that by the method according to the invention about 90% of high-boiling byproducts are converted with the following yields of desired products:

isoprene — 22.4% of converted high-boiling byproducts,
formaldehyde — 25.1% of converted high-boiling byproducts,
isobutylene — 7.5% of converted high-boiling byproducts.

In addition, the following products are obtained which may be used for conversion into desired products at isoprene plants:

methyldilydropyran — 7.1%
dimethyldioxane — 3.8%
methanol — 7.9%
trimethylcarbinol — 1.9%, so that additional yields of isoprene, formaldehyde and isobutylene are obtained which were not taken into account in this Example.

EXAMPLE 2

30 g. of aluminum oxide were charged into the first reactor and 60 g. of calcium-phosphate catalyst were charged into the second reactor. The conditions of processing high-boiling byproducts, which was carried out at atmospheric pressure, are given in Table 7, and the resulting products yields are given in Table 8.

TABLE 7
CONDITIONS OF PROCESSING HIGH BOILING BYPRODUCTS OVER ALUMINUM OXIDE AND CALCIUM-PHOSPHATE CATALYSTS

| Reactor in the flow direction of high boiling byproducts vapours | Temperature in the catalyst column, °C | | | High-boiling byproducts water weight ratio | Rate of feeding high-boiling byproducts g/h per 1 g of catalyst |
|---|---|---|---|---|---|
| | top | middle | bottom | | |
| 1st reactor with aluminum oxide | 268 | 255–256 | 290 | 1:1 | 1.0 |
| 2nd reactor with calcium-phosphate catalyst | 338 | 344 | 360 | 1:2 | 0.7 |

TABLE 8

YIELDS OF PRODUCTS IN SPLITTING HIGH-BOILING BYPRODUCTS OVER ALUMINUM OXIDE AND CALCIUM-PHOSPHATE CATALYSTS UNDER THE CONDITIONS SHOWN IN TABLE 7

| Starting high-boiling byproducts | | Reaction mixture | | | | | Converted | | Yield of products | % of Conversion of high-boiling byproducts |
|---|---|---|---|---|---|---|---|---|---|---|
| Components 1 | Content of mixture used for tests 2 | Components 3 | Organic layer,g 4 | Aqueous layer,g 5 | Gas, g 6 | Total, g 7 | g 8 | % 9 | g 10 | 11 |
| | | Carbon dioxide | — | — | 2.16 | 2.16 | | | 2.16 | 1.32 |
| | | Carbon oxide | — | — | 0.73 | 0.73 | | | 0.73 | 0.45 |
| | | Isobutylene | 3.74 | — | 9.20 | 12.94 | | | 12.94 | 7.93 |
| | | Amylenes | 1.38 | — | | 1.38 | | | 1.38 | 0.85 |
| | | Isoprene | 35.66 | — | 2.38 | 38.04 | | | 38.04 | 23.35 |
| | | Methanol | 3.59 | 4.35 | | 7.94 | | | 7.94 | 4.27 |
| | | Trimethylcarbinol | 0.31 | 3.16 | | 3.47 | | | 3.47 | 2.63 |
| Unsaturated alcohols C$_5$ | 5.38 | Unsaturated alcohols C$_5$ | 2.51 | 1.14 | | 3.65 | 1.73 | 32.2 | — | — |
| | | Methylenetetrahydropyran | 1.58 | — | | 1.58 | | | 1.58 | 0.97 |
| | | Methylhydropyran | 10.39 | 2.70 | | 13.09 | | | 13.09 | 8.03 |
| | | p-Xylene | 0.29 | — | | 0.29 | | | 0.29 | 0.18 |
| | | Dimethyldioxane | 2.56 | 2.96 | | 5.52 | | | 5.52 | 3.38 |
| Methylvinyldioxane | 1.01 | Methylvinyldioxane | 0.85 | — | — | 0.85 | 0.16 | 15.9 | — | — |
| Methylbutandiol ether | 2.79 | Methylbutandiol and Trimethylcarbinol ether | — | 2.85 | | 2.85 | — | — | 0.06 | 0.04 |
| Pyran alcohol | 5.08 | Pyran alcohol | 0.54 | 3.16 | | 3.70 | 1.38 | 27.2 | — | — |
| Methylbutandiol | 21.27 | Methylbutandiol | 0.36 | 0.78 | | 1.14 | 20.13 | 95.0 | — | — |
| Dioxane alcohol ethers | 10.75 | Dioxane alcohol ethers | 2.36 | 3.57 | | 5.93 | 4.82 | 44.8 | — | — |
| Dioxane alcohol formals | 6.96 | Dioxane alcohol formals | 0.41 | 1.14 | | 1.55 | 5.41 | 77.8 | — | — |
| Dioxane alcohols | 87.49 | Dioxane alcohols | 0.67 | 1.86 | | 2.53 | 84.96 | 97.0 | — | — |
| Total of unidentified compounds | 13.66 | Total of unidentified products | 11.58 | 3.63 | | 15.21 | — | — | 1.55 | 0.95 |
| Heavy unidentified compounds | 50.30 | Heavy unidentified compounds | 5.86 | — | | 5.86 | 44.44 | 88.5 | — | — |
| Formaldehyde | 2.94 | Formaldehyde | 4.36 | 39.49 | | 43.85 | | | 40.91 | 25.10 |
| Total of high-boiling byproducts used in test | 207.63 | | | | | | | | | |
| Water | 422.37 | Water | 0.5 | 447.41 | | 447.91 | | | 25.54 | 15.65 |
| | | Losses | — | — | | 7.83 | | | 7.83 | 4.80 |
| Total | 630.0 | Total | 89.5 | 518.2 | 14.47 | 630.0 | 163.03 | 82.5 | 163.03 | 100.0 |

The content of unsaturated alcohols in the final mixture is also negligible 3.65/630 100 = 0.52% which cannot appreciably lower the yield of isoprene on rectifying liquid reaction products due to chemical reactions.

The degree of conversion of high-boiling byproducts is more than 80%.

The yields of the desired products are as follows:

isoprene — 23.3% of converted high-boiling byproducts, formaldehyde — 25.1% of converted high-boiling byproducts, isobutylene — 7-9% of converted high-boiling byproducts In addition, the following products which are processed at isoprene plants into desired products are obtained:

methyldihydropyran — 8.0% dimethyldioxane — 3.4% methanol — 4.8% trimethylcarbinol — 2.6%

All remaining products may also be recycled for further processing into isoprene, formaldehyde and isobutylene.

What is claimed is:

1. A method of processing high-boiling byproducts obtained at the first stage of isoprene production by the dioxane method into isoprene, isobutylene and formaldehyde comprising catalytically splitting said byproducts in the vapour phase in the presence of water with a weight ratio therebetween of 1:1+2, respectively, at 250°–290° C over aluminium oxide as catalyst to obtain a vapour mixture; catalytically splitting said vapour mixture over calcium-phosphate catalyst at 315°–360° C to obtain a reaction mixture containing isoprene, isobutylene and formaldehyde.

* * * * *